United States Patent [19]

Palsrok et al.

[11] Patent Number: 4,826,486

[45] Date of Patent: May 2, 1989

[54] IV CONNECTOR LOCK AND STABILIZER

[75] Inventors: Gary Palsrok; Bonnie Palsrok, both of Traverse City, Mich.

[73] Assignee: Dale Medical Products, Inc., Plainville, Mass.

[21] Appl. No.: 86,894

[22] Filed: Aug. 18, 1987

Related U.S. Application Data

[63] Continuation-in-part of Ser. No. 940,440, Dec. 10, 1986.

[51] Int. Cl.4 .............................................. F16J 15/00
[52] U.S. Cl. .................................... 604/174; 604/905; 128/DIG. 26; 285/82; 285/364; 285/407; 285/420; 24/339
[58] Field of Search ............................ 604/174, 905; 128/DIG. 26; 285/82, 114, 305, 337, 340, 364, 374, 403, 407, 420; 24/339, 346

[56] References Cited

U.S. PATENT DOCUMENTS

| | | | |
|---|---|---|---|
| 805,579 | 11/1905 | Patchen | 285/114 |
| 1,310,627 | 7/1919 | McEvilly | 285/114 |
| 2,691,201 | 10/1954 | Matthews | 285/420 |
| 3,479,069 | 11/1969 | Sedam | 285/364 |
| 3,881,753 | 5/1975 | Bochory | 285/82 |
| 4,224,937 | 9/1980 | Gordon | 128/DIG. 26 |
| 4,230,109 | 10/1980 | Geiss | 604/280 |
| 4,333,505 | 6/1982 | Jones et al. | 604/905 |
| 4,704,177 | 11/1987 | Vaillancourt | 128/DIG. 26 |

Primary Examiner—Stephen C. Pellegrino
Assistant Examiner—Ralph Lewis
Attorney, Agent, or Firm—Schiller, Pandiscio & Kusmer

[57] ABSTRACT

An IV lock for preventing IV connectors from separating. The IV lock has two split-fork locks at each end for releasably securing a male IV fitting or connector to the IV lock and for releasably securing a catheter to the IV lock. The IV lock may also include a snap-fit clamp intermediate the two split-fork locks for securing an intermediate connector coupled between the male IV fitting and the catheter fitting from moving laterally and axially relative to its length. The male IV fitting and catheter are prevented from moving axially and transversely of their length when secured in the IV lock.

11 Claims, 1 Drawing Sheet

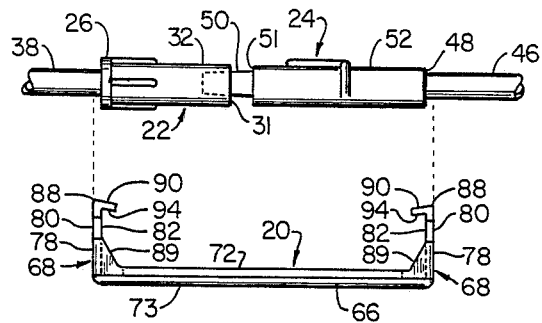
Fig. 1
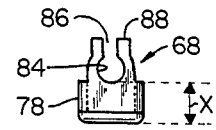
Fig. 2
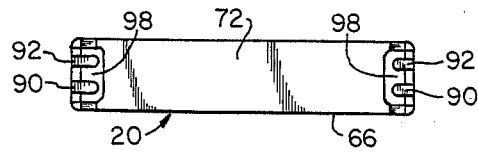
Fig. 3
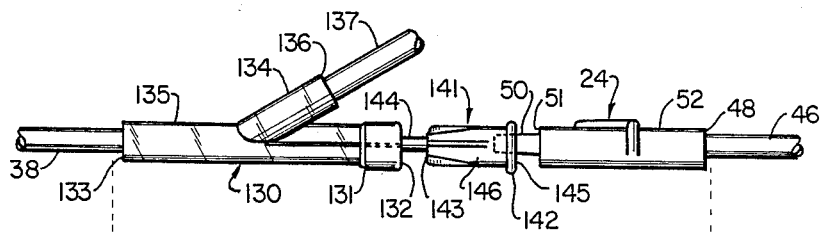
Fig. 4
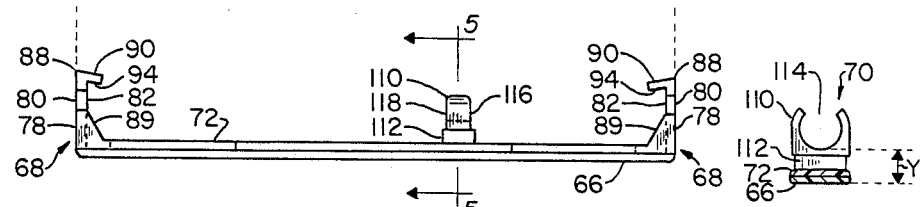
Fig. 5 (right) / Fig. 4 (left)
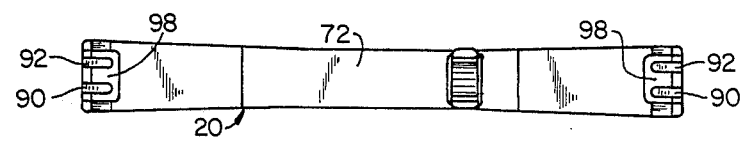
Fig. 6

IV CONNECTOR LOCK AND STABILIZER

This application is a continuation-in-part of U.S. application Ser. No. 940,440 filed on Dec. 10, 1986 and now pending.

This invention relates to medical apparatus used in administering intravenous fluid to a patient, and more particularly to a bracket for securing a male intravenous fitting to a female intravenous catheter.

As is well known by health care professionals and others associated with the health care field, intravenous (hereinafter "IV") fluid may typically be administered through a catheter inserted into a vein. The catheter is coupled to a male IV fitting that is connected by IV tubing to a supply of IV fluid. Not infrequently, the male IV fitting may become separated from the catheter, causing leakage of intravenous fluid. Separated IV lines may also cause hemorrhaging in the patient and may provide a site from which infectious germs and other contaminants may enter the patient's body. Air may also enter the patient's circulatory system when the connection between the male IV fitting and catheter is broken. If an embolism develops in the patient's circulatory system due to this introduction of air, cardiac damage, paralysis, coma or even death may result.

The problem of decoupling also exists at the site of the connectors used in extension tubing sets. Such extension tubing sets are frequently positioned in "free-swinging" portions of the line. By "free-swinging" it is meant that the IV line is not secured to a fixed object. Free-swinging lines are desirable in that they permit the health care professionals to move the line out of the way for routine patient care. However, such lines are frequently positioned where they aren't expected to be located and they may be inadvertently pulled with a sufficient force to cause decoupling.

In addition to the problems set forth above, a disconnected IV tube often creates additional work for health care personnel. For instance, it typically takes ten to fifteen minutes to change a leaky IV connection and five to ten minutes to replace IV fluid-soaked bed sheets.

Several methods of, and apparatus for, securing a male IV fitting to an IV catheter have been developed. In one known method, after the catheter has been inserted in the patient's vein, the male IV fitting is inserted in the catheter so as to frictionally engage the latter and establish a fluid-tight seal between the male IV fitting and the catheter. Then the entire assembly is bonded by adhesive tape and is secured to the patient, also by adhesive tape. This procedure is relatively slow and does not couple the catheter to the male IV fitting as securely as may be desired. Alternatively, IV connection locks such as those marketed under the trademark Luer Lock or such as those described in U.S. Pat. No. 4,224,937 have been used to secure male IV fittings to catheters. Luer Lock-type IV connector locks have been known to torque the cannula in a manner causing skin breakdown. Also, Luer Lock-type connectors on occasion are softened by the patient's body temperature resulting in leakage at the junction between the male IV fitting and the catheter The IV connector lock of U.S. Pat. No. 4,224,937 is designed to lock only the catheter hub, and not the male IV connector, to the base of the lock. As such, the male IV fitting may tend to separate from the catheter resulting in leakage of IV fluid. Another disadvantage of certain known IV connector locks is that they are designed to receive the catheter and male IV fitting of only one specific type of IV system. Other known IV connector locks suffer from the disadvantage of being relatively expensive.

The primary object of the present invention is to overcome the disadvantages and problems of known IV connector locks set forth above.

Another primary object of the present invention is to provide an IV connector lock for coupling a male IV fitting to a catheter in a manner substantially eliminating the possibility of the fitting becoming inadvertently decoupled from the catheter.

Other objects of the invention include providing an IV connector lock that (1) fits smoothly on an IV line in a manner avoiding the application of pressure which might restrict flow, (2) fits a variety of IV systems, (3) supports a needle head at the same angle at which it was inserted into a "Y" connector, (4) permits the male IV fitting to be connected to and disconnected from the catheter without causing discomfort to the patient and (5) locks both the male IV fitting and the catheter, when secured together, to the IV connector lock.

A further object of the invention is to provide an IV lock for tubing connectors, secondary line connectors and piggyback connectors which prevents both transverse and axial movement. For secondary line connectors in which a needle is connected to a "Y" connector, a lateral lock collar is provided to keep the needle holder stable and thus prevent decoupling.

An additional object is to provide a connector which fulfills the foregoing objectives and is designed to be relatively inexpensive to manufacture and assemble. The connector may be designed for one time use and thus discarded after the tubings are changed.

Other objects of the invention will in part be obvious and will in part appear hereinafter. The invention accordingly comprises the product possessing the features, properties and relation of components described hereinafter, and the scope of the application of which will be indicated in the claims.

The IV connector lock and stabilizer of the present invention comprises a bracket having a base, a first lock mounted to one end of the base for releasably gripping a conventional male IV fitting, a second lock mounted to the opposite end of the base for releasably gripping a conventional IV catheter fluidly coupled to said male IV fitting. In an alternate embodiment, a support lock is positioned near the center of the connector lock for stabilizing a needle inserted into a "Y" connector.

These and various other advantages and features of novelty which characterize the invention are pointed out with particularity in the claims annexed hereto and forming a part hereof. However, for a fuller understanding of the nature and objects of the present invention, reference should be had to the following detailed description and to the accompanying drawings in which there is illustrated a preferred embodiment of the invention.

FIG. 1 is a side view of the bracket of the invention and an extension tubing lock;

FIG. 2 is an end view of the bracket of the invention;

FIG. 3 is a plan view of the bracket of the invention;

FIG. 4 is a side view of an alternate embodiment of the invention showing the bracket and a "Y" connector and needle;

FIG. 5 is a side view of the bracket shown in FIG. 4 along line 5; and

FIG. 6 is a plan view of the bracket shown in FIG. 4.

Referring now to FIG. 1, the present invention is an IV lock 20 for ensuring that the two portions of a extension tubing connects remains coupled. The extension tubing connector is composed of a female catheter 22 and male fitting 24 which do not constitute part of the invention.

Catheter 22 is a conventional catheter used to administer intravenous fluid to a patient. Catheter 22 is hollow and comprises a hub 26 situated between and connecting outgoing tubing 38 and cylinder 32. The receiving end 31 of the cylinder 32 has opening 30 for receiving the male fitting 24.

Although catheters of the type identified at 22 are produced by a variety of manufactures, such as Abbott Laboratories of Abbott Park, Ill., certain portions of the catheter are made by most of the various manufacturers to standard dimensions.

Male IV fitting 24 is also a conventional fitting of the type manufactured by Abbott Laboratories and others. Fitting 24 is translucent and hollow. A hollow frusto-conically tapering front portion 50 is secured to the front end 51 of fitting 24. The outside diameter and taper of front portion 50 are selected so that when inserted in aperture 30 at the rear end 31 of catheter 22, front portion 50 will form a fluid-tight, friction fit with the interior of cylinder 32. IV tube 46 is fluidly connected to fitting 24 at its rear end 48. IV tube 46 usually has an outside diameter in the range of from 0.210" to 0.260" and is available from a variety of manufacturers, such as Abbott Laboratories. Rear portion 52 of fitting 24 is formed so that the outside diameter of the former is radially spaced a selected distance from the outside diameter of IV tube 46. As with catheter 22, certain portions of IV fitting 24 are made to standard dimensions by most manufacturers.

IV lock 20, as illustrated in FIGS. 1, 2 and 3, comprises base 66 and two split-fork locks 68. IV lock 20 is preferably made from a material that is relatively rigid while also being slightly resilient, such as polystyrene. Known molding procedures, such as hot-air injection molding, may be satisfactorily employed in the fabrication of IV lock 20.

Base 66 comprises substantially flat top surface 72 and an opposing substantially flat bottom surface 73. Base 66 has a thickness sufficient to ensure that the base remains substantially inflexible over its length. The length of base 66 corresponds to the distance between outgoing tubing 38 and incoming tubing 46 when IV clamp 24 is fluidly coupled to catheter 22, as described more fully below.

A split-fork lock 68 is secured to base 66 at each end. Lock 68 comprises base portion 78, the latter having opposed, parallel, flat surface 80 and 82 (FIG. 2) formed thereon. Surfaces 80 and 82 form an approximately 90° angle with respect to top surface 72. Surface 89, located beneath flat surface 82, extends at an oblique angle from the base 66 and serves to reinforce the connection of the split fork lock 68 to base 66. Aperture 84 and slot 86 are formed extending entirely through base portion 78. Slot 86 is connected to aperture 84 so that the aperture opens upwardly toward top edge 88 of lock 68. The diameter of aperture 84 is substantially identical to the outside diameter of IV tube 46 and the width of slot 86 is slightly less than the outside diameter of IV tube 46. The base of aperture 84 is spaced a distance x (FIG. 2) from the bottom surface of base portion 66.

Fingers 90 and 92 (FIG. 3) are coupled to base portion 78 at top edge 88 on opposite sides of slot 86 and extend toward the opposite end of base 66. Fingers 90 and 92 have flat underside surfaces 94 (FIG. 1) and 96 which form an acute angle with surfaces 80 and 82, respectively, that ranges between 81 and 87 degrees, with 84 degrees being the preferred angle. The vertical distance between the center of aperture 84 and the underside surfaces 94 and 96 where they join surface 82 is substantially identical to the radial spacing between the center of IV tube 46 and the outer surface of rear portion 52. Slot 98 extends between fingers 90 and 92 and is coupled to slot 86 and has the same width as slot 86.

In an alternate preferred embodiment shown in FIGS. 4-6, the IV lock 20 has an additional part, namely, snap-fit clamp 70. This embodiment is directed to securing a "Y" connector 130 used in extension tubing. The "Y" connector 130 and needle holder 141 are standard parts and do not constitute part of the invention.

The needle holder 141 has a shoulder 142, a body 146 and a front end 143. The needle 144 is molded into the front end 143. The shoulder 142 is located at the needle holder's rear end 145. The rear end 145 has an aperture for receiving a male fitting 24. This is the same male fitting as shown in FIG. 1.

The "Y" connector 130 has a rubber port seal 131 at the incoming end 132 of the "Y" connector. The port seal covers and seals the incoming end 132. The outgoing end 133 of the "Y" connector 130 has an outgoing tubing 38 which serves the same function in the catheter 22 (FIG. 1). Arm 134 extends from the main portion 135 of connector 130 and forms the arm of the "Y". The arm end 136 has an opening (not shown) for receiving a second incoming tube 137. Parts 134, 136 and 137 correspond respectively to parts 52, 48 and 46 of the male fitting 24 shown in FIGS. 1 or 2.

Snap-fit clamp 70 comprises cylinder 110 secured via portion 112 to base 66. The inside diameter of cylinder 110 is substantially identical to the outside diameter of needle holder 141. The axial length of cylinder 110 is either equal to or less than the length of the needle holder's body 146. An opening 114 is formed in the top portion of ring 110. Opening 114 spans an approximately 90 degrees segment of the circumference of ring 110. The bottommost portion of the interior of cylinder 110 is spaced a distance y (FIG. 5) from the bottom surface of base 66. As described more fully below, distance y is approximately equal to distance x (FIG. 2).

A pair of vertically extending walls 116 and 118 define the ends of cylinder 110. Walls 116 and 118 are spaced from cylinder 110 along the length of base 66 a distance slightly smaller than the axial spacing between shoulder 142 and rear end 145 of needle holder 141.

The present invention is used in the following manner for securing a catheter inserted in a patient to an IV fitting adapted for attachment to a source of intravenous fluid. The catheter 22, which is connected to the venipuncture site, is connected to the fitting 24. This is accomplished by inserting front portion 50 of male fitting 24 at the rear end 31 of catheter 22 until a fluid-tight seal is achieved between front portion 50 and the interior of cylinder 32. When coupled together in this manner, intravenous fluid flows from the source thereof through IV tube 46, fitting 24, cylinder 32 and outgoing tubing 38 and into the patient. Next, IV tube 46 is forced through slots 86 and 98 until the IV tube is received in aperture 84. The split fork bends inward and downward from the force and is designed to be of a material that is both lightweight and flexible. Since the outside diameter of tube 46 is slightly greater than the width of slots 86 and 98, the IV tube flattens slightly as it is forced through the slots. Coupled fitting 24, needle holder 141 and "Y" connector 130 are then moved axially until rear end 48 engages surface 82. In this position the outer surface of rear portion 52 engages the underside surfaces 94 and 96 of fingers 90 and 92, respectively, due to the vertical placement of aperture 84 on portion 78.

The needle holder 141 is then forced into the snap-clamp 70. The needle holder body 146 is then urged through opening 114 into cylinder 110. IV lock 20 is made from a slightly resilient material so that the walls of cylinder 110 adjacent opening 114 will spread apart slightly as needle holder 141 is forced through the opening. When needle holder 141 is received in cylinder 110, the inner surface of cylinder 110 engages the outer surface of needle holder 141 so as to releasably secure the latter in cylinder 110. When needle holder 141 is secured in this manner, needle holder 146 is received in the space between cylinder 110 and walls 116 and 118.

The outgoing end 133 of the "Y" connector 130 is then positioned in a manner very similar to the rear end 48 of the IV fitting 24. The outgoing tube 38 is forced through slots 86 and 98 until the IV tube is received in aperture 84. Once again, since the outside diameter of outgoing tube 38 is slightly greater than the width of slots 86 and 98, the outgoing IV tube flattens slightly as it is forced through the slots. The coupled fitting 24, needle holder 141 and "Y" connector 130 are then aligned axially until the outgoing end 133 is positioned near or against surface 82.

As noted above, the base of aperture 84 on each end of the IV lock 20 is spaced distance x from the bottom of base 66 and the base of the interior of cylinder 110 is spaced distance y from the bottom of base 66. Distance x is approximately equal to distance y with the result that the "Y" connector 130, fitting 24 and needle holder 141 are supported at the same angle. The needle 144 is thus positioned so that it runs parallel to the main portion 135 of the "Y" connector. Thus, substantially the entire length of the underneath surfaces 94 and 96 of fingers 90 and 92 of locks 68 engage, respectively, (1) the outer surface of rear portion 52 of fitting 24 and (2) the outer surface of catheter 22 or portion 135 of "Y" connector 130. Also, surfaces 82 of locks 68 engage, respectively, (1) rear end 48 of fitting 24 and (2) the rear end of catheter 22 or rear end 133 of Y connector 130. By this engagement, fitting 24, and catheter 22 or Y connector 13 are positively restrained (i.e., physically blocked as opposed to frictionally restrained) from moving transversely of their length.

"Y" connector 130 is similarly prevented from moving transversely of its length when secured in aperture 84 and the connector fits tightly in the IV lock 20. The snap-fit clamp 70 prevents the needle holder 141 from moving transversely of its length and also prevents the "Y" connector from moving laterally when the IV line is inadvertently tugged. The snap-fit clamp 70 prevents the needle holder 141 from swinging fully in the base causing the needle 144 to break away and allow free flow in the IV feeding system. Under normal conditions, the walls of cylinder 110 adjacent opening 114 prevent needle holder 141 from moving relative to IV lock 20, the needle holder 141 may be pulled through opening 114 with sufficient force to deform the walls of cylinder 110 adjacent the opening. Typically, the force required to remove "Y" connector 141 from IV lock 20 or cause enough lateral movement to cause the needle to break is greater than the force a patient or health care professional might accidentally exert on the connector.

Catheter 22 or "Y" connector 141 and fitting 24 are also prevented from moving axially relative to one another when secured in IV lock 20. As noted above, with conventional IV fittings, when catheter 22 is coupled to fitting 24, as in embodiment 1, or the "Y" connector 130, needle holder 141 and fitting 24 are connected, as in embodiment 2, the distance between ends 26 or 133 and 48 is standardized. The length of base 66 is selected so that the distance between base portion 78 and cylinder 110 corresponds to this standardized distance. Consequently, when connector is secured in IV lock 20, rear end 48 engages surface 82, end 26 or 133 engages the opposite surface 82 and in embodiment 2 the needle holder is engaged in cylinder 110. In this position the coupled catheter 22 and fitting 24 are positively restrained (i.e., physically blocked as opposed to frictionally restrained) from moving axially apart from one another.

It is to be understood, however, since changes may be made in the above apparatus, especially in matters of shape and size, without departing from the scope of the invention herein involved, it is intended that all matter contained in the above description or shown in the accompanying drawings shall be interpreted in an illustrative and not in a limiting sense. The present invention is incidated by the broad general meaning of the terms in which the appended claims are expressed.

What is claimed is:

1. A bracket for preventing separation and fluid leakage between an elongate incoming intravenous connector fitting fluidly couple with an elongate outgoing intravenous connector fitting, wherein said bracket comprises:

an elongated base having a first end, a second end, and a substantially flat surface;

first clamp means attached to said first end of said base for releasably locking said incoming connector fitting to said base so that said incoming connector fitting is blocked from moving transversely away from said base and axially along the axis of elongation of said base away from said second end toward said first end;

second clamp means attached to said second end of said base for releasably locking said outgoing connector fitting to said base so that said outgoing connector fitting is blocked from moving transversely away from said base and axially along the axis of elongation of said base away from said first end toward said second end;

wherein said first clamp member comprises;

(a) a first member attached at its bottom end to said first end of said base, said first member having a substantially flat inner surface extending so as to form an angle of approximately 90 degrees with respect to said substantially flat surface of said base, said first member having a top end opposite said bottom end;

(b) an aperture extending through said first member;

(c) a slot extending through said first member coupled with said aperture so as to split said first member into first and second sections, said slot intersecting said top end of said first member;

(d) first and second fingers attached, respectively, to said first and second sections so as to extend toward said second end of said base; and (e) a slot extending between said first and second fingers coupled with said slot in said first member.

2. A bracket for preventing separation and fluid leakage between an elongate incoming intravenous connector fitting fluidly coupled with an elongate outgoing intravenous connector fitting, wherein said bracket comprises:

an elongated base having a first end, a second end, and a substantially flat surface;

first clamp means attached to said first end of said base for releasably locking said incoming connector fitting to said base so that said incoming connector fitting is blocked from moving transversely away from said base and axially along the axis of elongation of said base away from said second end toward said first end;

second clamp means attached to said second end of said base for releasably locking said outgoing connector fitting to said base so that said outgoing connector fitting is blocked from moving transversely away from said base and axially along the axis of elongation of said base away from said first end toward said second end;

wherein said second clamp member comprises:

(a) a second member attached at its bottom end to said second end of said base, said second member having a substantially flat inner surface extending so as to form an angle of approximately 90 degrees with respect to said substantially flat surface of said base, said second member having a top end opposite said bottom end;

(b) an aperture extending through said second member;

(c) a slot extending through said second member coupled with said aperture so as to split said second member into first and second sections, said slot intersecting said top end of said second member;

(d) first and second fingers attached, respectively, to said first and second sections so as to extend toward said first end of said base; and (e) a slot extending between said first and second fingers coupled with said slot in said first member.

3. A bracket for preventing separation and fluid leakage between an elongate incoming intravenous connector fitting fluidly coupled with an elongate outgoing intravenous connector fitting, wherein said bracket comprises:

an elongated base having a first end, a second end, and a substantially flat surface;

first clamp means attached to said first end of said base for releasably locking said incoming connector fitting to said base so that said incoming connector fitting is blocked from moving transversely away from said base and axially along the axis of elongation of said base away from said second end toward said first end;

second clamp means attached to said second end of said base for releasably locking said outgoing connector fitting to said base so that said outgoing connector fitting is blocked from moving transversely away from said base and axially along the axis of elongation of said base away from said first end toward said second end;

wherein bracket further comprises:

(a) third clamp means mounted to said base for releasably locking an intermediate connector fitting positioned between and fluidly coupled with said incoming connector fitting and said outgoing connector fitting so as to restrain said intermediate connector fitting from moving axially toward and away from said first and second ends and transversely toward and away from said base.

4. A bracket according to claim 3 in which said third clamp means comprises a cylindrical member attached to said base, said cylindrical member having (1) approximately 25% of the entire circumference of said cylindrical member removed to form an open top portion and (2) an inner wall.

5. A bracket according to claim 4 in which said third clamp means further comprises a base portion that positions said cylindrical member away from said base so that the inner wall of said cylindrical member is axially aligned with said apertures of said first and second clamp means.

6. A bracket according to claim 4 or 5 in which said intermediate connector fitting comprises a needle holder, further wherein said third clamp means is adapted to restrain said needle holder from moving axially toward and away from said first end and said second end and transversely toward and away from said base.

7. A bracket according to claim 1, 2 or 3 which said bracket is made of a resilient, dense synthetic polymer.

8. A bracket according to claim 7 in which said polymer is nylon.

9. A bracket for preventing separation and fluid leakage between an elongate incoming intravenous connector fitting fluidly coupled with an elongate outgoing intravenous connector fitting, said incoming connector fitting comprising a first shoulder and said outgoing connector fitting comprising a second shoulder, said first and second shoulders being spaced apart from one another a selected distance when said incoming connector fitting is fluidly coupled with said outgoing connector fitting, wherein said bracket comprises:

an elongated base having a first end, a second end, and a substantially flat surface;

first clamp means attached to said first end of said base for releasably locking said incoming connector fitting is blocked from moving transversely away from said base and axially along the axis of elongation of said base away from said second end toward said first end;

second clamp means attached to said second end of said base for releasably locking said outgoing connector fitting to said base so that said outgoing connector fitting is blocked from moving transversely away from said base and axially along the axis of elongation of said base away from said first end toward said second end;

wherein said first clamp member comprises:

(a) a first member attached at its bottom end to said first end of said base, said first member having a substantially flat inner surface extending so as to form an angle of approximately 90 degrees with respect to said substantially flat surface of said base, said first member having a top end opposite said bottom end;

(b) an aperture extending through said first member;

(c) a slot extending through said first member coupled with said aperture so as to split said first member into first and second sections, said slot intersecting said top end of said first member;

(d) first and second fingers attached, respectively, to said first and second sections so a to extend toward said second end of said base; and (e) a slot extending between said first and second fingers coupled with said slot in said first member;

wherein said first clamp means is substantially spaced from said second clamp means said selected distance so that said first clamp means is positioned to engage the first shoulder of the incoming connector fitting and said second clamp means is positioned to engage the second shoulder of the outgoing connector fitting when said incoming and outgoing connector fittings are locked to said bracket.

10. A bracket for preventing separation and fluid leakage between an elongate incoming intravenous connector fitting fluidly coupled with an elongate outgoing intravenous connector fitting, said incoming connector fitting comprising a first shoulder and said outgoing connector fitting comprising a second shoulder, said first and second shoulder being spaced apart from one another a selected distance when said incoming connector fitting is fluidly coupled with said outgoing connector fitting, wherein said bracket comprises:

an elongated base having a first end, a second end, and a substantially flat surface;

first clamp means attached to said first end of said base for releasably locking said incoming connector fitting to said base so that said incoming connector fitting is blocked from moving transversely away from said base and axially along the axis of elongation of said base away from said second end toward said first end;

second clamp means attached to said second end of said base for releasably locking said outgoing connector fitting to said base so that said outgoing connector fitting is blocked from moving transversely away from said base and axially along the axis of elongation of said base away from said first end toward said second end;

wherein said second clamp member comprises:

(a) a second member attached at its bottom end to said second end of said base, said second member having a substantially flat inner surface extending so as to form an angle of approximately 90 degrees with respect to said substantially flat surface of said base, said second member having a top end opposite said bottom end;

(b) an aperture extending through said second member;

(c) a slot extending through said second member coupled with said aperture so as to split said second member into first and second sections, said slot intersecting said top end of said second member;

(d) first and second fingers attached, respectively, to said first and second sections so as to extend toward said first end of said base; and (e) a slot extending between said first and second fingers coupled with said slot in said first member; and wherein said first clamp means is substantially spaced from said second clamp means said selected distance so that said first clamp means is positioned to engage the first shoulder of the incoming connector fitting and said second clamp means is positioned to engage the second shoulder of the outgoing connector fitting when said incoming and outgoing connector fittings are locked to said Blackest.

11. A bracket for preventing separation and fluid leakage between an elongate incoming intravenous connector fitting fluidly coupled with an elongate outgoing intravenous connector fitting, said incoming connector fitting comprising a first shoulder and said outgoing connector fitting comprising a second shoulder, said first an second shoulder being spaced apart from one another a selected distance when said incoming connector fitting is fluidly coupled with said outgoing connector fitting, wherein said bracket comprises:

an elongated base having a first end, a second end, and a substantially flat surface;

first clamp means attached to said first end of said base for releasably locking said incoming connector fitting to said base so that said incoming connector fitting is blocked from moving transversely away from said base and axially along the axis of elongation of said base away from said second end toward said first end;

second clamp means attached to said second end of said base for releasably locking said outgoing connector fitting to said base so that said outgoing connector fitting is blocked from moving transversely away from said base and axially along the axis of elongation of said base away from said first end toward said second end;

third clamp means mounted to said base for releasably locking an intermediate connector fitting positioned between and fluidly coupled with said incoming connector fitting and said outgoing connector fitting so as to restrain said intermediate connector fitting from moving axially toward and away from said first and second ends and transversely toward and away from said base; and wherein said first clamp means is substantially spaced from said second clamp means said selected distance so that said first clamp means is positioned to engage the first shoulder of the incoming connector fitting and said second clamp means is positioned to engage the second shoulder of the outgoing connector fitting when said incoming and outgoing connector fittings are locked to said bracket.

* * * * *

UNITED STATES PATENT AND TRADEMARK OFFICE
CERTIFICATE OF CORRECTION

PATENT NO. : 4,826,486

DATED : May 2, 1989

INVENTOR(S) : Gary Palsrok, et al.

It is certified that error appears in the above-identified patent and that said Letters Patent is hereby corrected as shown below:

Claim 1, column 6, line 33, delete "couple" and substitute therefor -- coupled --;

Claim 1, column 6, line 53, delete ";" and substitute therefor -- : --;

Claim 3, column 7, line 64, after "wherein" insert -- said --;

Claim 7, column 8, line 24, after "3" insert -- in --;

Claim 9, column 8, line 42, after "fitting" insert -- to said base so that said incoming connector fitting --;

Claim 9, column 8, line 67, delete "a" and substitute therefor -- as --;

Claim 10, column 9, line 17, delete "shoulder" and substitute therefor -- shoulders --;

Claim 10, column 10, line 11, delete "Black-" and substitute therefor -- bracket --;

Claim 10, column 10, line 12, delete "est";

Claim 11, column 10, line 19, delete "an" and substitute therefor -- and --; and

UNITED STATES PATENT AND TRADEMARK OFFICE
CERTIFICATE OF CORRECTION

PATENT NO. : 4,826,486

DATED : May 2, 1989

INVENTOR(S) : Gary Palsrok, et al.

It is certified that error appears in the above-identified patent and that said Letters Patent is hereby corrected as shown below:

Claim 11, column 10, line 19, delete "shoulder" and substitute therefor -- shoulders --.

Signed and Sealed this

Ninth Day of January, 1990

*Attest:*

JEFFREY M. SAMUELS

*Attesting Officer*     *Acting Commissioner of Patents and Trademarks*